(12) United States Patent
Okamura et al.

(10) Patent No.: US 7,006,599 B2
(45) Date of Patent: Feb. 28, 2006

(54) RADIOGRAPHIC APPARATUS

(75) Inventors: Shoichi Okamura, Nara-ken (JP); Toshinori Yoshimuta, Osaka-fu (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 10/853,357

(22) Filed: May 26, 2004

(65) Prior Publication Data

US 2004/0258207 A1 Dec. 23, 2004

(30) Foreign Application Priority Data

Jun. 20, 2003 (JP) .............................. 2003-176040

(51) Int. Cl.
*H05G 1/64* (2006.01)

(52) U.S. Cl. .................... 378/98.11; 378/98.8; 378/19; 250/370.08; 250/370.09

(58) Field of Classification Search .................... 378/4, 378/19, 62, 98.8, 98.11, 98.12, 207; 250/370.08, 250/370.09, 370.11
See application file for complete search history.

(56) References Cited

U.S. PATENT DOCUMENTS

| | | | | |
|---|---|---|---|---|
| 5,249,123 | A | 9/1993 | Hsieh | 378/19 |
| 5,452,338 | A * | 9/1995 | Granfors et al. | 378/98.11 |
| 5,517,544 | A | 5/1996 | Levinson | 378/4 |
| 5,644,610 | A * | 7/1997 | Crawford et al. | 378/19 |
| 6,265,720 | B1 * | 7/2001 | Yamazaki et al. | 250/370.09 |
| 6,493,646 | B1 * | 12/2002 | Hsieh et al. | 702/104 |

* cited by examiner

*Primary Examiner*—Edward J. Glick
*Assistant Examiner*—Courtney Thomas
(74) *Attorney, Agent, or Firm*—Rader, Fishman & Grauer PLLC (57) ABSTRACT

A radiographic apparatus removes lag-behind parts from radiation detection signals taken from an FPD as X rays are emitted from an X-ray tube, on an assumption that the lag-behind part included in each X-ray detection signal is due to an impulse response formed of exponential functions, N in number, with different attenuation time constants. The lag-behind parts are removed by using impulse responses corresponding to variations in the sensor temperature of the FPD. X-ray images are created from corrected radiation detection signals with the lag-behind parts removed therefrom.

21 Claims, 8 Drawing Sheets

RADIOGRAPHIC APPARATUS

BACKGROUND OF THE INVENTION (1) Field of the Invention

This invention relates to a radiographic apparatus for medical or industrial use, for obtaining radiographic images based on radiation detection signals fetched at predetermined sampling time intervals by a signal sampling device from a radiation detecting device as radiation is emitted from a radiation emitting device. More particularly, the invention relates to a technique for fully eliminating time lags, due to the radiation detecting device, of the radiation detection signals taken from the radiation detecting device.

(2) Description of the Related Art

In a medical fluoroscopic apparatus which is a typical example of radiographic apparatus, a flat panel X-ray detector (hereinafter called "FPD" as appropriate) has recently been used as an X-ray detecting device for detecting X-ray penetration images of a patient resulting from X-ray emission from an X-ray tube. The FPD includes numerous semiconductor or other X-ray detecting elements arranged longitudinally and transversely on an X-ray detecting surface.

That is, in the fluoroscopic apparatus, X-ray detection signals for one X-ray image are taken at sampling time intervals from the FPD as a patient is irradiated with X rays from the X-ray tube. The fluoroscopic apparatus is constructed to obtain, based on the X-ray detection signals, an X-ray image corresponding to an X-ray penetration image of the patient for every period between sampling intervals. The use of the FPD is advantageous in terms of apparatus construction and image processing since the FPD is lighter and less prone to complicated detecting distortions than the image intensifier used heretofore.

However, the FPD has a drawback of causing time lags whose adverse influence appears in X-ray images. Specifically, when X-ray detection signals are taken from the FPD at short sampling time intervals, the remainder of a signal not picked up adds to a next X-ray detection signal as a lag-behind part. Thus, where X-ray detection signals for one image are taken from the FPD at 30 sampling intervals per second to create X-ray images for dynamic display, the lag-behind part appears as an after-image on a preceding screen to produce a double image. This results in an inconvenience such as blurring of dynamic images.

U.S. Pat. No. 5,249,123 discloses a proposal to solve the problem of the time lag caused by the FPD in acquiring computer tomographic images (CT images). This proposed technique employs a computation for eliminating a lag-behind part from each of radiation detection signals taken from an FPD at sampling time intervals $\Delta t$.

That is, in the above U.S. patent, a lag-behind part included in each of the radiation detection signals taken at the sampling time intervals is assumed due to an impulse response formed of a plurality of exponential functions, and the following equation is used to derive radiation detection signal $x_k$ with a lag-behind part removed from radiation detection signal $y_k$:

$$x_k = \left[ y_k - \sum_{n=1}^{N} \{\alpha_n \cdot [1 - \exp(T_n)] \cdot \exp(T_n) \cdot S_{nk}\} \right] / \sum_{n=1}^{N} \beta_n$$

in which $T_n = -\Delta t/\tau_n$, $S_{nk} = X_{k-1} + \exp(T_n) \cdot S_{n(k-1)}$, and $\beta_n = \alpha_n \cdot [1 - \exp(T_n)]$, where $\Delta t$: sampling intervals;

k: subscript representing a k-th point of time in a sampling time series;

N: the number of exponential functions with different time constants forming the impulse response;

n: subscript representing one of the exponential functions forming the impulse response;

$\alpha_n$: intensity of exponential function n; and $\tau_n$: attenuation time constant of exponential function n.

Inventors herein have tried the computation technique proposed in the above U.S. patent. However, the only result obtained is that the above technique cannot avoid artifacts due to the time lag and satisfactory X-ray images cannot be obtained. It has been confirmed that the time lag due to the FPD is not eliminated.

Further, U.S. Pat. No. 5,517,544 discloses a different proposal to solve the problem of the time lag caused by the FPD in acquiring CT images. This technique assumes a time lag of the FPD to be approximated by one exponential function, and removes a lag-behind part from a radiation detection signal by computation. Inventors herein have carefully reviewed the computation technique proposed in this U.S. patent. It has been found, however, that it is impossible for one exponential function to approximate the time lag of the FPD, and the time lag is not eliminated by this technique, either.

SUMMARY OF THE INVENTION

This invention has been made having regard to the state of the art noted above, and its object is to provide a radiographic apparatus for fully eliminating time lags, due to a radiation detecting device, of radiation detection signals taken from the radiation detecting device.

The following technique is conceivable to solve the above problem. In dealing with the time lag of the FPD, this technique removes a lag-behind part due to an impulse response based on the following recursive equations A–C:

$$X_k = Y_k - \sum_{n=1}^{N} \{\alpha_n \cdot [1 - \exp(T_n)] \cdot \exp(T_n) \cdot S_{nk}\} \quad \text{A}$$

$T_n = -\Delta t/\tau_n$ B $$S_{nk} = X_{k-1} + \exp(T_n) \cdot S_{n(k-1)} \quad \text{C}$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

In the above recursive computation, coefficients of the impulse response of the FPD, N, $\alpha_n$ and $\tau_n$, are determined in advance. With the coefficients fixed, X-ray detection signal $Y_k$ is applied to equations A–C, thereby obtaining a lag-free X-ray detection signal $X_k$.

Figure 10:
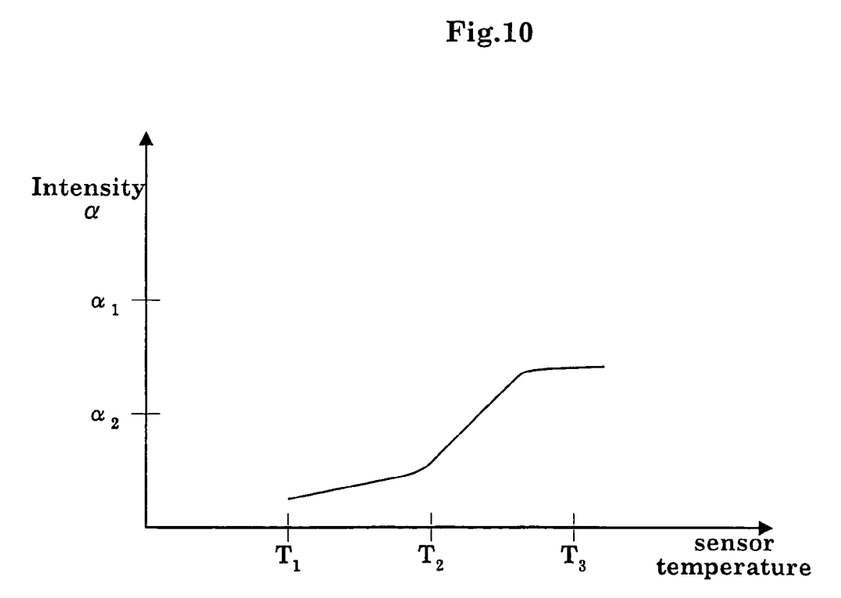
FIG. 10 is a view schematically showing a relationship between sensor temperature and impulse response coefficient.

In practice, however, the impulse response of the FPD is not invariable. Inventors have attained the following findings as a result of experiment conducted under various conditions to determine the cause of the variable impulse response. In the experiment, the sensor temperature of the FPD was changed to vary the impulse response. FIG. 10 is a view schematically illustrating the experiment, in which the horizontal axis represents sensor temperature and the vertical axis intensity $\alpha_n$ of exponential function n, with the other impulse response coefficients N and $\tau_n$ fixed.

As seen from FIG. 10, the intensity $\alpha_n$ is variable with the sensor temperature. When the sensor temperature changes, with $\alpha_n$ and N fixed, $\tau_n$ will also change. When the sensor temperature changes, with $\alpha_n$ and $\tau_n$ fixed, N will also change. This sensor temperature is variable with the temperature of the room where the sensor of the FPD is present. Thus, even with the same FPD, the impulse response coefficients N, $\alpha_n$ and $\tau_n$ are variable every moment. It has been found, therefore, that the impulse response is variable with the sensor temperature.

Consequently, when impulse response coefficients obtained under a sensor temperature condition in time of detection differ from those derived beforehand, an X-ray detection signal $X_k$ with a lag-behind part removed from the signal $Y_k$ cannot be derived accurately from the recursive equations A–C noted above. In other words, an X-ray detection signal $X_k$ may be determined accurately by removing a lag-behind part based on impulse response coefficients obtained under a sensor temperature condition in time of detection.

Based on the above findings, this invention provides a radiographic apparatus having a radiation emitting device for emitting radiation toward an object under examination, a radiation detecting device for detecting radiation transmitted through the object under examination, and a signal sampling device for taking radiation detection signals from the radiation detecting device at predetermined sampling time intervals, for obtaining radiographic images based on the radiation detection signals outputted from the radiation detecting device at the predetermined sampling time intervals as radiation is emitted to the object under examination, the apparatus comprising:

a temperature measuring device for measuring temperature of the radiation detecting device; and a time lag removing device for removing lag-behind parts from the radiation detection signals by a recursive computation, on an assumption that a lag-behind part included in each of the radiation detection signals taken at the predetermined sampling time intervals is due to an impulse response formed of one exponential function or a plurality of exponential functions with different attenuation time constants;

wherein the time lag removing device is arranged to determine the impulse response based on a result provided by the temperature measuring device, and obtain a corrected radiation detection signal by removing the lag-behind part based on the impulse response corresponding to the result.

With the radiographic apparatus according to this invention, radiation detection signals are outputted from the radiation detecting device at predetermined sampling time intervals as radiation is emitted from the radiation emitting device to an object under examination. A lag-behind part included in each of the radiation detection signals is regarded as due to an impulse response formed of one exponential function or a plurality of exponential functions with different attenuation time constants. The time lag removing device removes such lag-behind parts by using impulse responses corresponding to variations in the temperature of the radiation detecting device. A radiographic image is obtained from corrected radiation detection signals with the lag-behind parts removed.

Thus, the radiographic apparatus according to the invention, the impulse response is determined based on the result provided by the temperature measuring device when the time lag removing device computes a corrected radiation detection signal by removing a lag-behind part from each radiation detection signal. The computation is performed based on the impulse response corresponding to the result of temperature measurement. The corrected radiation detection signal computed in this way is free from errors due to variations in the temperature of the radiation detecting device, and has the lag-behind part fully removed therefrom. Even with variations in the temperature of the radiation detecting device, an accurate impulse response is used at all times to remove effectively a lag-behind part due to the radiation detecting device, thereby obtaining corrected radiation detection signals with high accuracy.

In the above radiographic apparatus, the temperature measuring device may be arranged to measure temperature automatically at every predetermined time, or upon the operator's instruction for temperature measurement, or automatically before an actual emission of radiation performed upon an instruction for emitting radiation.

With the automatic temperature measurement, temperature may be measured accurately at all times without possibilities of the operator forgetting to measure temperatures or making errors.

In the former, automatic temperature measurement, the predetermined time may be set by inputting a point of time for measuring the temperature. In another example of automatic temperature measurement, the predetermined time may be set at time intervals having a fixed value (e.g. every 30 minutes). In a further example of automatic temperature measurement, the predetermined time may be set by schedule information containing points of time. In a still further example of automatic temperature measurement, the predetermined time may be set by inputting a passage of time from a current point of time (e.g. five minutes from now).

In the radiographic apparatus, the radiation detecting device, for example, is a flat panel X-ray detector having numerous X-ray detecting elements arranged longitudinally and transversely on an X-ray detecting surface.

In the radiographic apparatus, preferably, impulse response coefficients corresponding to temperatures are determined based on a predetermined relationship between the temperature of the radiation detecting device and the impulse response coefficients, and results of measurement by the temperature measuring device.

In the radiographic apparatus, the radiation detecting device may be a flat panel X-ray detector having numerous X-ray detecting elements arranged longitudinally and transversely on a radiation detecting surface, the flat panel X-ray detector including a semiconductor film which is an X-ray sensitive film for generating carriers in response to incident X rays, a voltage application electrode disposed on an X-ray incident surface of the semiconductor film, carrier collection electrodes arranged on a non-incident surface of the semiconductor film and acting as part of the X-ray detecting elements, and a glass plate having the carrier collection electrodes vapor-deposited thereon, the temperature measuring device including a thermistor applied to the glass plate, and a controller for reading a resistance of the thermistor.

With this temperature measuring device, a change of the sensor temperature changes the temperature of the glass plate which in turn changes the resistance of the thermistor applied to the surface of glass plate. The controller reads a current value variable under a fixed voltage applied to the thermistor, to obtain a change in the resistance of the thermistor, thereby ultimately obtaining a sensor temperature.

In the above temperature measuring device, the thermistor may be applied centrally of the glass plate, or a plurality of thermistors may be applied to several positions on the glass plate.

In another example, the radiation detecting device is a flat panel X-ray detector having numerous X-ray detecting elements arranged longitudinally and transversely on a radiation detecting surface, the temperature measuring device comprising resisting elements provided for the X-ray detecting elements, respectively.

The temperature measuring device in the above example measures the temperature of each detecting element by reading the resisting element provided therefor.

In the radiographic apparatus, the time lag removing device, preferably, is arranged to perform the recursive computation for removing the lag-behind part from each of the radiation detection signals, based on the following equations A–C:

$$X_k = Y_k - \sum_{n=1}^{N} \{\alpha_n \cdot [1 - \exp(T_n)] \cdot \exp(T_n) \cdot S_{nk}\} \quad \text{A}$$

$T_n = -\Delta t / \tau_n B$ $S_{nk} = X_{k-1} + \exp(T_n) \cdot S_{n(k-1)}$     C where Δt: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

With this construction, the second term in equation A $$"\sum_{n=1}^{N} \{\alpha_n \cdot [1 - \exp(T_n)] \cdot \exp(T_n) \cdot S_{nk}\}"$$

corresponds to the lag-behind part. Thus, the corrected, lag-free X-ray detection signal $X_k$ may be derived promptly from equations A–C constituting a compact recurrence formula.

This invention is applicable to a medical apparatus, and an apparatus for industrial use as well. An example of medical apparatus is a fluoroscopic apparatus. Another example of medical apparatus is an X-ray CT apparatus. An example of apparatus for industrial use is a nondestructive inspecting apparatus.

The radiation detecting device is not limited to a particular location for installation. The radiation detecting device may be placed inside a housing, with a resin poured into the housing to mold the radiation detecting device. Then, the radiation detecting device may be enclosed in the resin and embedded in the housing.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

First Embodiment

Figure 1:
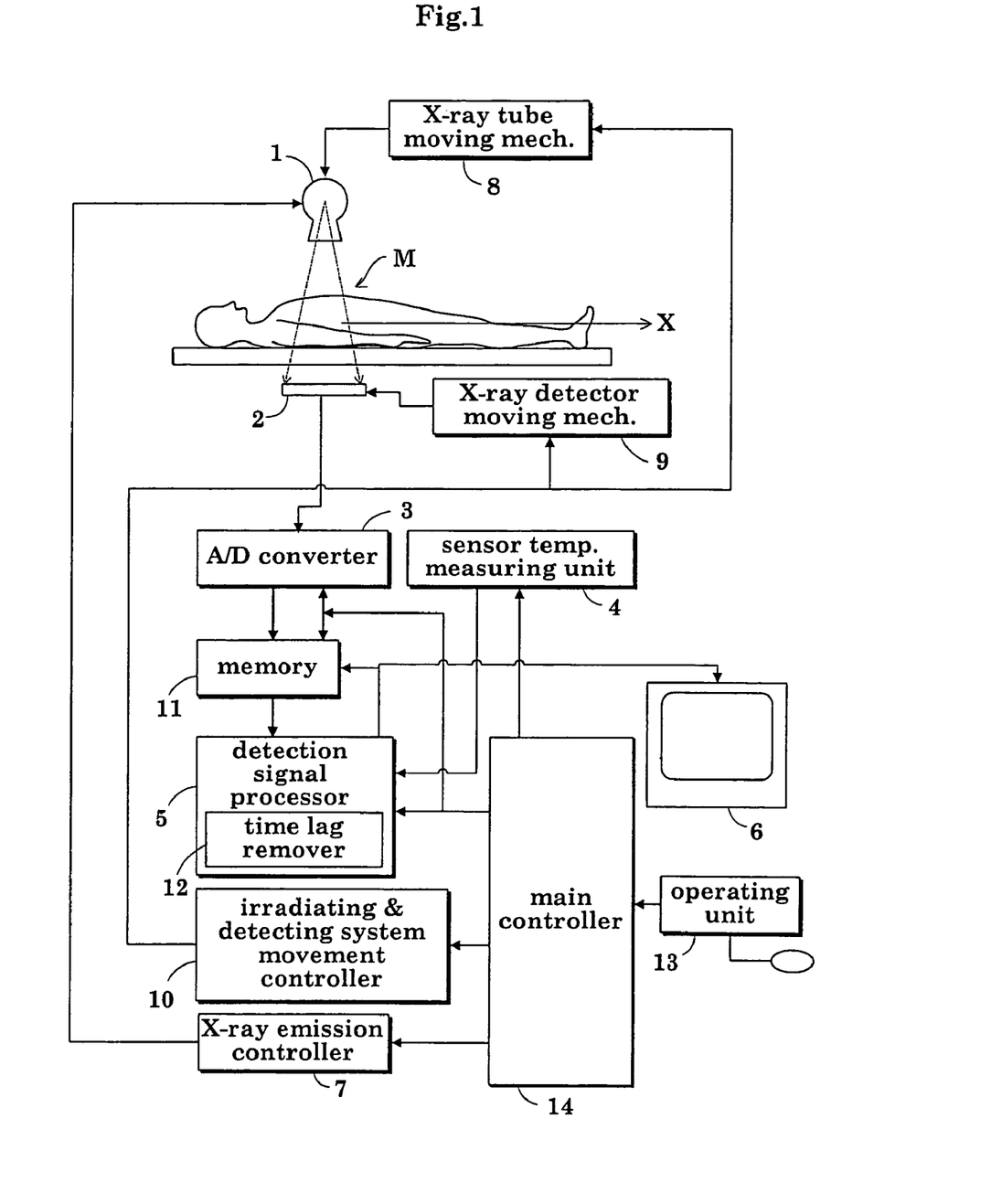
FIG. 1 is a block diagram showing an overall construction of a fluoroscopic apparatus in a first embodiment of the invention.

FIG. 1 is a block diagram showing an overall construction of a fluoroscopic apparatus in a first embodiment.

As shown in FIG. 1, the fluoroscopic apparatus includes an X-ray tube (radiation emitting device) 1 for emitting X rays toward a patient M, an FPD (radiation detecting device) 2 for detecting X rays transmitted through the patient M, an analog-to-digital converter (signal sampling device) 3 for digitizing X-ray detection signals (radiation detection signals) taken from the FPD (flat panel X-ray detector) 2 at predetermined sampling time intervals Δt, a sensor temperature measuring unit (temperature measuring device) 4 for measuring a sensor temperature of FPD 2, a detection signal processor 5 for creating X-ray images based on X-ray detection signals outputted from the analog-to-digital converter 3 and measurements provided by the sensor temperature measuring unit 4, and an image monitor 6 for displaying the X-ray images created by the detection signal processor 5. That is, the apparatus is constructed to acquire X-ray images from the X-ray detection signals taken from the FPD 2 by the analog-to-digital converter 3 as the patient M is irradiated with X rays, and display the acquired X-ray images on the screen of the image monitor 6. Each component of the apparatus in the first embodiment will particularly be described hereinafter.

The X-ray tube 1 and FPD 2 are opposed to each other across the patient M. In time of X-ray radiography, the X-ray tube 1 is controlled by an X-ray emission controller 7 to emit X rays in the form of a cone beam to the patient M. At the same time, penetration X-ray images of the patient M produced by the X-ray emission are projected to an X-ray detecting surface of FPD 2.

The X-ray tube 1 and FPD 2 are movable back and forth along the patient M by an X-ray tube moving mechanism 8 and an X-ray detector moving mechanism 9, respectively. In moving the X-ray tube 1 and FPD 2, the X-ray tube moving mechanism 8 and X-ray detector moving mechanism 9 are controlled by an irradiating and detecting system movement controller 10 to move the X-ray tube 1 and FPD 2 together as opposed to each other, with the center of emission of X rays constantly in agreement with the center of the X-ray detecting surface of FPD 2. Of course, movement of the X-ray tube 1 and FPD 2 results in variations in the position of the patient M irradiated with X rays, hence movement of a radiographed site.

Figure 2:
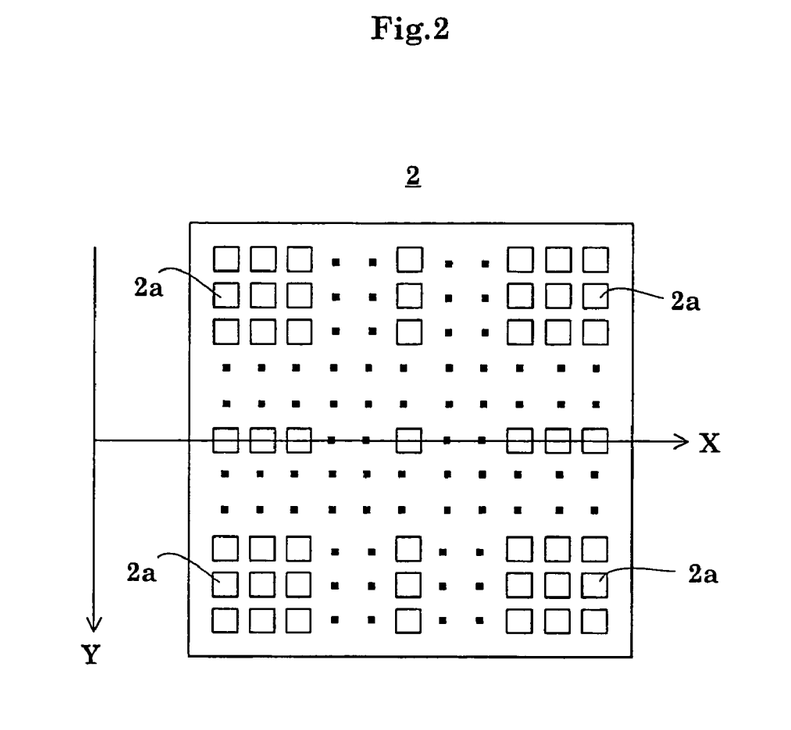
FIG. 2 is a plan view of an FPD used in the first embodiment.

As shown in FIG. 2, the FPD 2 has numerous X-ray detecting elements 2a arranged longitudinally and transversely along the direction X of the body axis of patient M and the direction Y perpendicular to the body axis, on the X-ray detecting surface to which penetration X-ray images from the patient M are projected. For example, X-ray detecting elements 2a are arranged to form a matrix of 1536 by 1536 on the X-ray detecting surface about 30 cm long and 30 cm wide. Each X-ray detecting element 2a of FPD 2 corresponds to one pixel in an X-ray image created by the detection signal processor 5. Based on the X-ray detection signals taken from the FPD 2, the detection signal processor 5 creates an X-ray image corresponding to a penetration X-ray image projected to the X-ray detecting surface.

Figure 4:
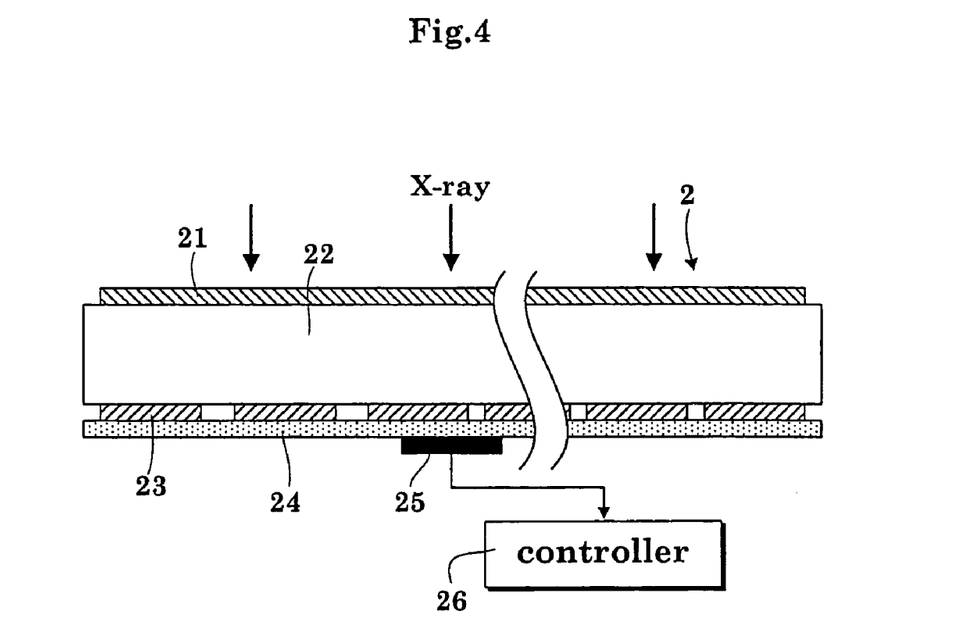
FIG. 4 is a view showing a positional relationship between a cross section and a sensor temperature measuring unit of the FPD used in the first embodiment.

The FPD 2 has a cross section as shown in FIG. 4. The FPD 2 includes a semiconductor film 22 which is an X-ray sensitive film (e.g. an amorphous Se thick film) for generating carriers in response to incident X rays, a voltage application electrode 21 disposed on the X-ray incident surface of the semiconductor film 22, carrier collection electrodes 23 arranged on the non-incident surface of the semiconductor film 22 and acting as part of the X-ray detecting elements 2a of FPD 2, and a glass plate 24 having the carrier collection electrodes 23 vapor-deposited thereon. The glass plate 24 has also a thermistor 25 applied thereto to act as part of the sensor temperature measuring unit 4.

The analog-to-digital converter 3 continually takes X-ray detection signals for each X-ray image at sampling time intervals $\Delta t$, and stores the X-ray detection signals for X-ray image creation in a memory 11 disposed downstream of the converter 3. An operation for sampling (extracting) the X-ray detection signals is started before X-ray irradiation.

Figure 3:
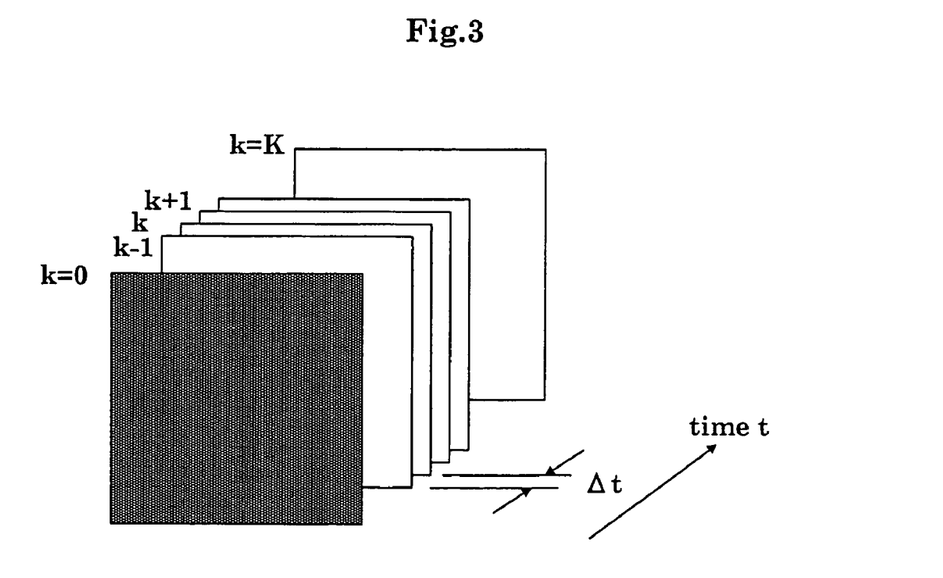
FIG. 3 is a schematic view showing a state of sampling X-ray detection signals during X-ray radiography in the first embodiment.

That is, as shown in FIG. 3, all X-ray detection signals for a penetration X-ray image are collected at each period between the sampling intervals $\Delta t$, and are successively stored in the memory 11. The sampling of X-ray detection signals by the analog-to-digital converter 3 before an emission of X rays may be started manually by the operator or automatically as interlocked with a command for X-ray emission.

The sensor temperature measuring unit 4 obtains a sensor temperature of FPD 2 on an instruction from the operator or at every predetermined time, and transmits sensor temperature data to the detection signal processor 5. The sensor temperature measuring unit 4 includes the thermistor 25 and a controller 26, shown in FIG. 4, for reading a resistance of the thermistor 25. A change of the sensor temperature changes the temperature of glass plate 24 which in turn changes the resistance of the thermistor 25 applied to the surface of glass plate 24. The controller 26 reads a current value variable under a fixed voltage applied to the thermistor 25, to obtain a change in the resistance of the thermistor 25, thereby ultimately obtaining a sensor temperature.

As shown in FIG. 1, the fluoroscopic apparatus in the first embodiment includes a time lag remover 12 for computing corrected radiation detection signals free from time lags. A time lag is removed from each X-ray detection signal by a recursive computation based on an assumption that a lag-behind part included in each of the X-ray detection signals taken at the sampling time intervals from the FPD 2 is due to an impulse response formed of a single exponential function or a plurality of exponential functions with different attenuation time constants.

Figure 5:
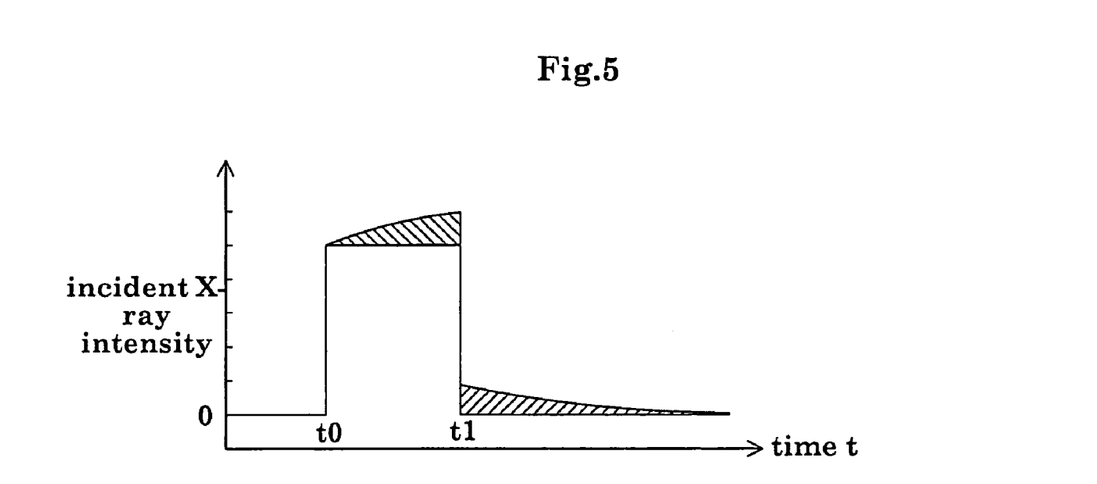
FIG. 5 is a view showing a time lag of a radiation detection signal.

With the FPD 2, an X-ray detection signal generated at each point of time, as shown in FIG. 5, includes signals corresponding to preceding X-ray emissions and remaining as a lag-behind part (hatched part). The time lag remover 12 removes this lag-behind part to produce a corrected, lag-free X-ray detection signal. Based on such lag-free X-ray detection signals, the detection signal processor 5 creates an X-ray image corresponding to a penetration X-ray image to be projected to the X-ray detecting surface.

Specifically, the time lag remover 12 performs a recursive computation processing for removing a lag-behind part from each X-ray detection signal by using the following equations A–C:

$$X_k = Y_k - \sum_{n=1}^{N} \{\alpha_n \cdot [1 - \exp(T_n)] \cdot \exp(T_n) \cdot S_{nk}\} \quad \text{A}$$

$$T_n = -\Delta t/\tau_n \quad \text{B}$$

$$S_{nk} = X_{k-1} + \exp(T_n) \cdot S_{n(k-1)} \quad \text{C}$$

where $\Delta t$: the sampling time interval;

k: a subscript representing a k-th point of time in a sampling time series;

$Y_k$: an X-ray detection signal taken at the k-th sampling time;

$X_k$: a corrected X-ray detection signal with a lag-behind part removed from the signal $Y_k$;

$X_{k-1}$: a signal $X_k$ taken at a preceding point of time;

$S_{n(k-1)}$: an $S_{nk}$ at a preceding point of time;

exp: an exponential function;

N: the number of exponential functions with different time constants forming the impulse response;

n: a subscript representing one of the exponential functions forming the impulse response;

$\alpha_n$: an intensity of exponential function n; and $\tau_n$: an attenuation time constant of exponential function n.

N, $\alpha_n$ and $\tau_n$ in particular are called "impulse response coefficients".

The second term in equation A $$"\sum_{n=1}^{N} \{\alpha_n \cdot [1 - \exp(T_n)] \cdot \exp(T_n) \cdot S_{nk}\}"$$

$\cdot \exp(T_n) \cdot S_{nk}\}$" corresponds to the lag-behind part. Thus, the apparatus in the first embodiment derives the corrected, lag-free X-ray detection signal $X_k$ promptly from equations A–C constituting a compact recurrence formula.

The impulse response of FPD 2 changes also with the sensor temperature of FPD 2. That is, the impulse response coefficients N, $\alpha_n$ and $\tau_n$ used in equations A and B change also with the sensor temperature. The detection signal processor 5 stores a relationship between the sensor temperature and the impulse response coefficients determined for the FPD 2 in advance (see FIG. 10, for example). The processor 5 receives results of measurement from the sensor temperature measuring unit 4, and causes the time lag remover 12 to remove time lags by using impulse response coefficients corresponding to the temperatures measured.

In the first embodiment, the analog-to-digital converter 3, detection signal processor 5, X-ray emission controller 7, irradiating and detecting system movement controller 10 and time lag remover 12 are operable on instructions and data inputted from an operating unit 13 or on various commands outputted from a main controller 14 with progress of X-ray radiography.

Next, an operation for performing X-ray radiography with the apparatus in the first embodiment will particularly be described with reference to the drawings.

Figure 6:
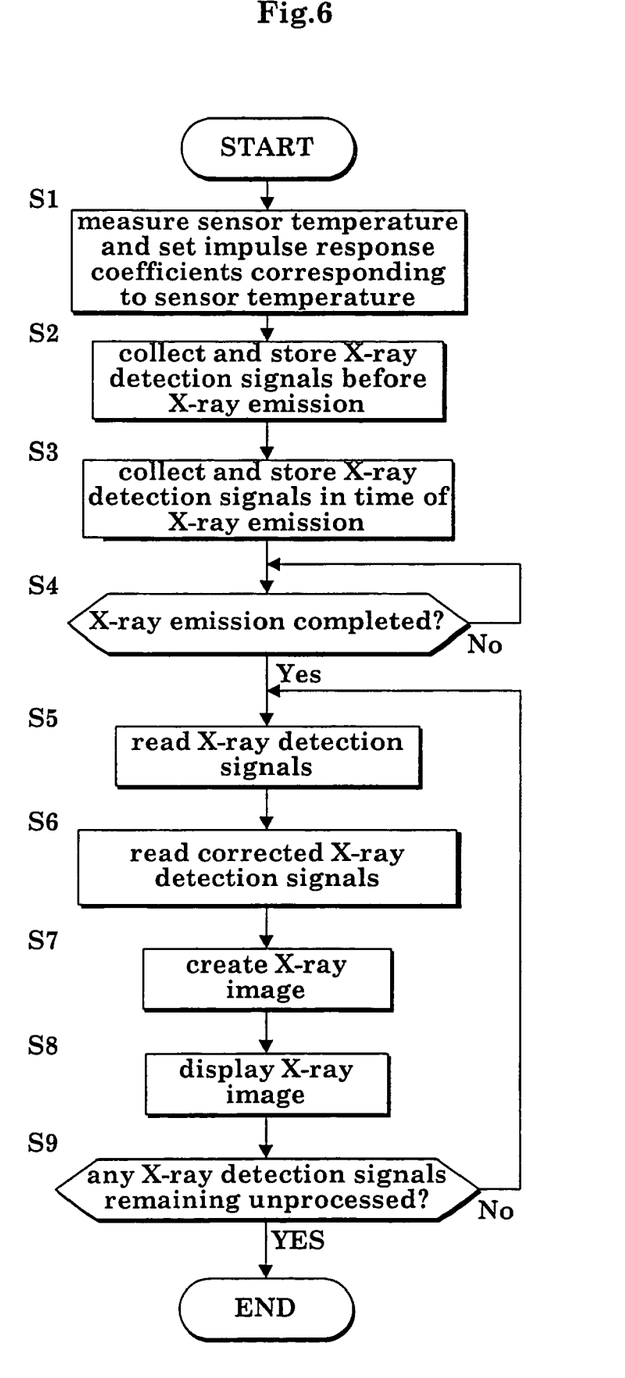
FIG. 6 is a flow chart showing a procedure of X-ray radiography in the first embodiment.

FIG. 6 is a flow chart showing a procedure of X-ray radiography in the first embodiment.

[Step S1] On an instruction of the operator or at every predetermined time, the sensor temperature measuring unit 4 measures the temperature of FPD 2 before X-ray emission, and transmits the sensor temperature to the detection signal processor 5. The detection signal processor 5 applies to the time lag remover 12 impulse response coefficients N, $\alpha_n$ and $\tau_n$ of FPD 2 corresponding to the sensor temperature received.

[Step S2] The analog-to-digital converter 3 starts taking X-ray detection signals $Y_k$ for one X-ray image from the FPD 2 at each period between the sampling time intervals $\Delta t$ (=1/30 second) before X-ray emission. The X-ray detection signals taken are stored in the memory 11.

[Step S3] In parallel with a continuous or intermittent X-ray emission to the patient M initiated by the operator, the analog-to-digital converter 3 continues taking X-ray detection signals $Y_k$ for one X-ray image at each period between the sampling time intervals $\Delta t$ and storing the signals in the memory 11.

[Step S4] When the X-ray emission is completed, the operation proceeds to step S5. When the X-ray emission is uncompleted, the operation returns to step S3.

[Step S5] X-ray detection signals $Y_k$ for one X-ray image collected in one sampling sequence are read from the memory 11.

[Step S6] The time lag remover 12 performs the recursive computation based on the equations A–C using the impulse response coefficients N, $\alpha_n$ and $\tau_n$ corresponding to the sensor temperature received from the sensor temperature measuring unit 4, and derives corrected X-ray detection signals $X_k$, i.e. pixel values, with lag-behind parts removed from the respective X-ray detection signals $Y_k$.

[Step S7] The detection signal processor 5 creates an X-ray image based on the corrected X-ray detection signals $X_k$ for one sampling sequence (for one X-ray image).

[Step S8] The X-ray image created is displayed on the image monitor 6.

[Step S9] When unprocessed X-ray detection signals $Y_k$ remain in the memory 11, the operation returns to step S5. When no unprocessed X-ray detection signals $Y_k$ remain, the X-ray radiography is ended.

In the first embodiment, the time lag remover 12 computes the corrected X-ray detection signals $X_k$ corresponding to the X-ray detection signals $Y_k$ for one X-ray image, and the detection signal processor 5 creates an X-ray image, both at each period between the sampling time intervals $\Delta t$ (=1/30 second). That is, the apparatus is constructed also for creating X-ray images one after another at a rate of about 30 images per second, and displaying the created X-ray images continuously. It is thus possible to perform a dynamic display of X-ray images.

Figure 8:
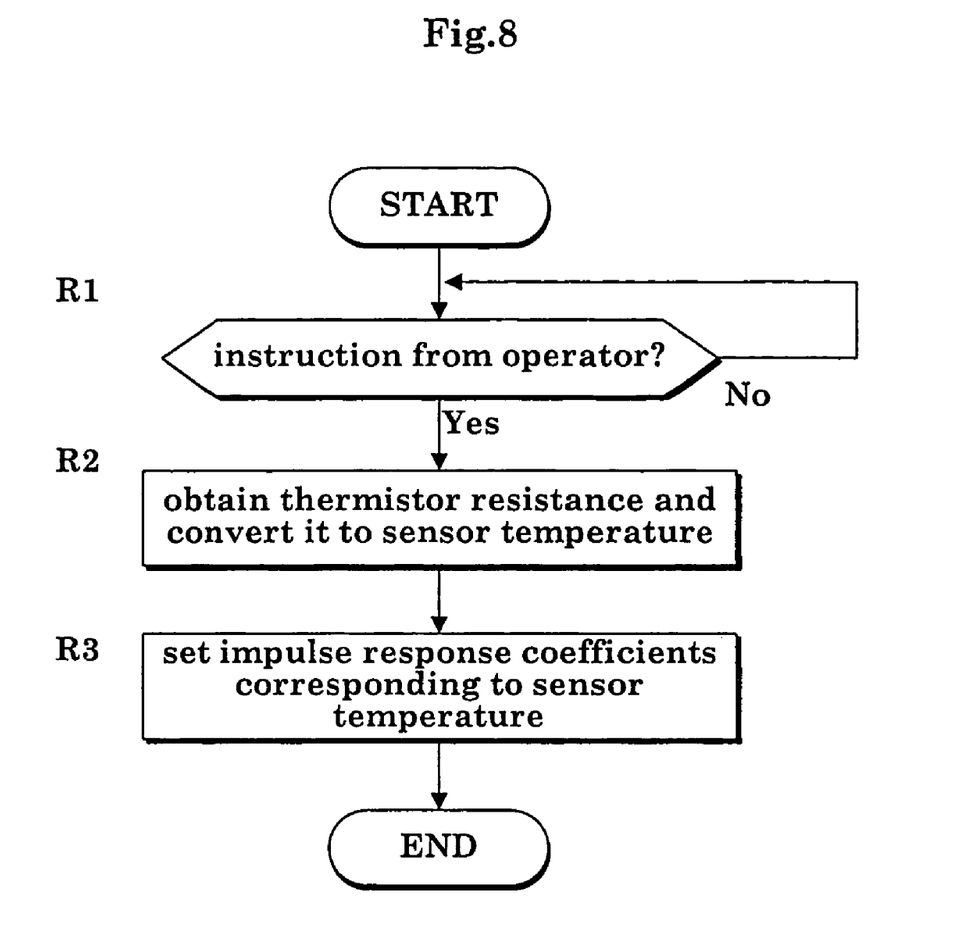
FIG. 8 is a flow chart showing an operation for setting a sensor temperature measurement and impulse response coefficients according to the sensor temperature in the first embodiment.

Next, the operations in the above step S1 of the sensor temperature measuring unit 4 and detection signal processor 5 will particularly be described. FIG. 8 is a flow chart showing an operation for setting a sensor temperature measurement and impulse response coefficients according to sensor temperatures in the first embodiment. [Step R1] The sensor temperature measuring unit 4 waits until an operator's instruction for sensor temperature measurement is received through the operating unit 13 and main controller 14.

[Step R2] Upon receipt of an instruction for sensor temperature measurement, the controller 26 of the sensor temperature measuring unit 4 measures the resistance of the thermistor 25, converts it to temperature data, and transmits the data to the detection signal processor 5.

[Step R3] The detection signal processor 5 gives the time lag remover 12 the impulse response coefficients N, $\alpha_n$ and $\tau_n$ of FPD 2 corresponding to the sensor temperature received from the sensor temperature measuring unit 4. Then, the operation returns to step R1 and waits for a next instruction.

Thereafter, the time lag remover 12 performs time lag removing computations using the impulse response coefficients corresponding to the latest sensor temperatures measured by the sensor temperature measuring unit 4.

Figure 7:
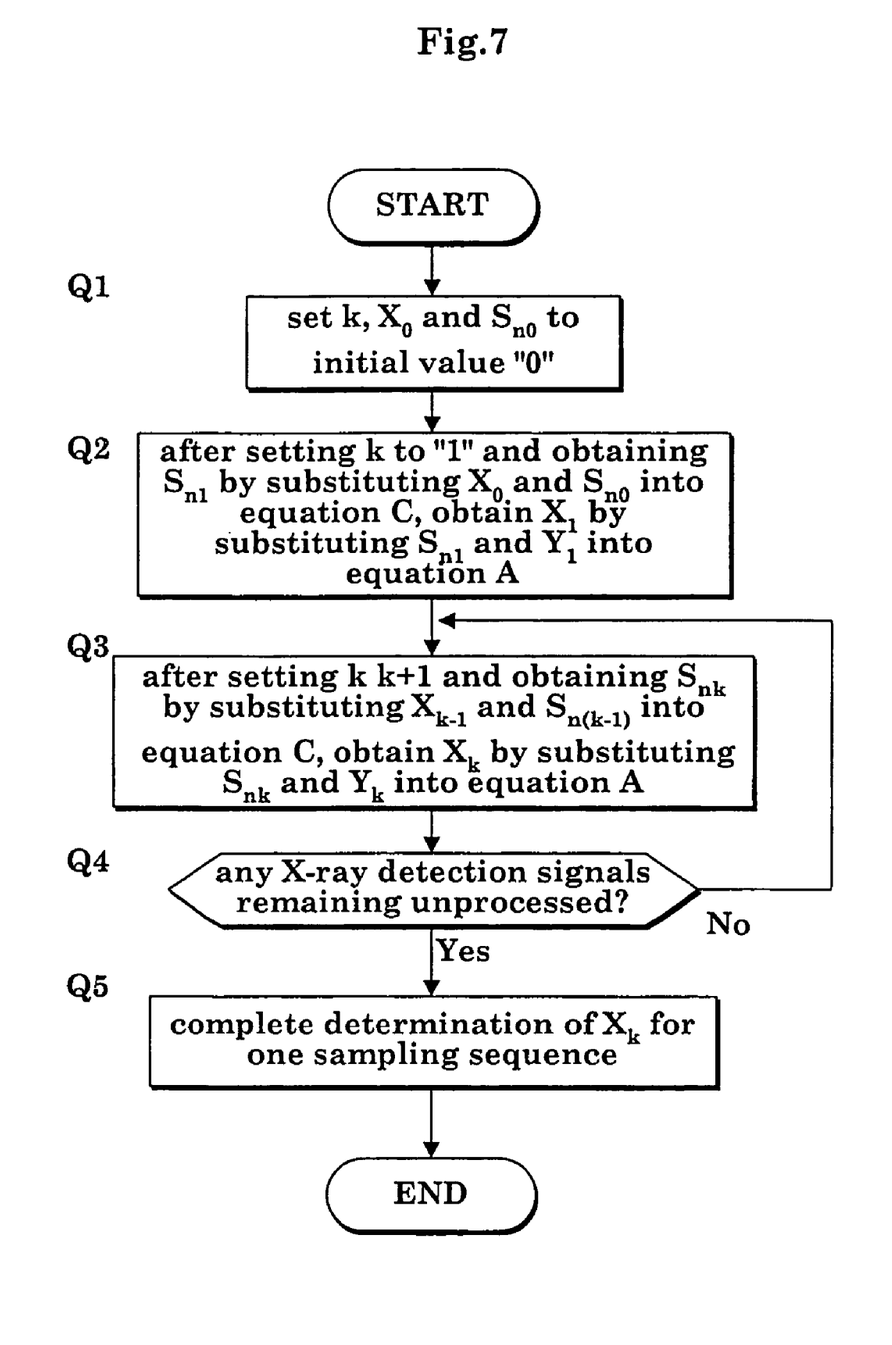
FIG. 7 is a flow chart showing a recursive computation process for time lag removal in the first embodiment.

Next, the process of recursive computation carried out in step S6 in FIG. 6 by the time lag remover 12 will be described with reference to FIG. 7. FIG. 7 is a flow chart showing a recursive computation process for time lag removal in the first embodiment

[Step Q1] A setting k=0 is made, and $X_0$=0 in equation A and $S_{n0}$=0 in equation C are set as initial values before X-ray emission. Where the number of exponential functions is three (N=3), $S_{10}$, $S_{20}$ and $S_{30}$ are all set to 0.

[Step Q2] In equations A and C, k=1 is set. $S_{11}$, $S_{21}$ and $S_{31}$ are derived from equation C, i.e. $S_{n1}=X_0+\exp(T_n)S_{n0}$. Further, corrected X-ray detection signal is obtained by substituting $S_{11}$, $S_{21}$ and $S_{31}$ derived and X-ray detection signal $Y_1$ into equation A.

[Step Q3] After incrementing k by 1 (k=k+1) in equations A and C, $S_{1k}$, $S_{2k}$ and $S_{3k}$ are obtained by substituting $X_{k-1}$ of a preceding time into equation C. Further, corrected X-ray detection signal $X_k$ is obtained by substituting $S_{1k}$, $S_{2k}$ and $S_{3k}$ derived and X-ray detection signal $Y_k$ into equation A.

[Step Q4] When there remain unprocessed X-ray detection signals $Y_k$, the operation returns to step Q3. When no unprocessed X-ray detection signals $Y_k$ remain, the operation proceeds to step Q5.

[Step Q5] Corrected X-ray detection signals $X_k$ for one sampling sequence (for one X-ray image) are obtained to complete the recursive computation for the one sampling sequence.

According to the fluoroscopic apparatus in the first embodiment, as described above, impulse response coefficients corresponding to a sensor temperature are used when the time lag remover 12 computes a corrected X-ray detection signal by removing a lag-behind part from each X-ray detection signal by the recursive computation. Thus, corrected X-ray detection signals are obtained with high accuracy.

In the first embodiment, the sensor temperature is measured upon instructions from the operator. This invention is not limited to such measurement. The sensor temperature may be measured automatically before an actual emission of X rays upon instructions from the operator to emit X rays.

Second Embodiment

In the second embodiment, the sensor temperature is measured automatically at every predetermined time.

The second embodiment has the same features and functions as the first embodiment except that the sensor temperature is measured on instructions from the operator or at predetermined times. What is common with the first embodiment will not be described, but only the different aspects will be described by using FIG. 9.

Figure 9:
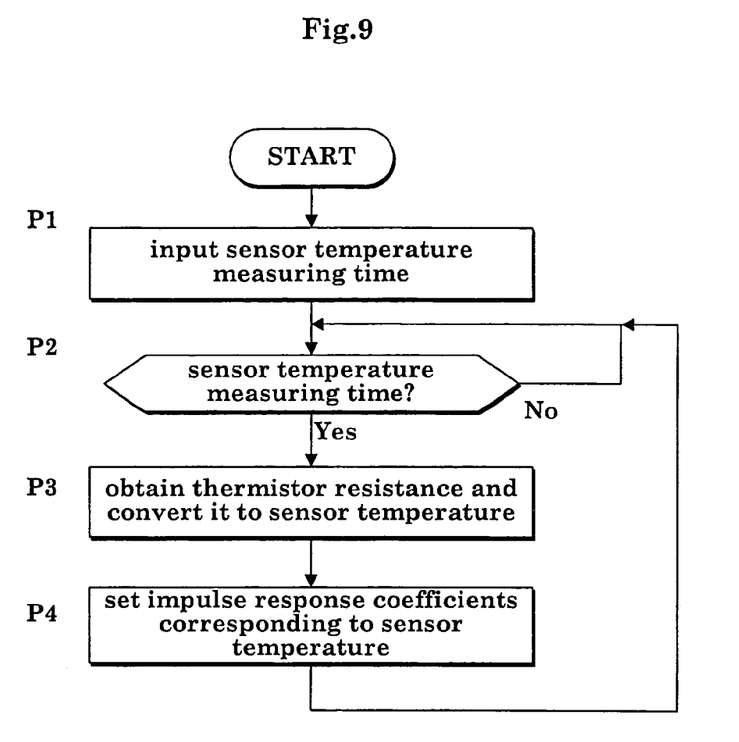
FIG. 9 is a flow chart showing an operation for setting a sensor temperature measurement and impulse response coefficients according to the sensor temperature in a second embodiment.

FIG. 9 is a flow chart showing an operation for setting a sensor temperature measurement and impulse response coefficients according to sensor temperatures in the second embodiment.

[Step P1] The operator inputs points of time for performing a sensor temperature measurement through the sensor temperature measuring unit 4, operating unit 13 and main controller 14.

[Step P2] The controller 26 of the sensor temperature measuring unit 4 checks whether a predetermined time has arrived.

[Step P3] At the predetermined time, the controller 26 of the sensor temperature measuring unit 4 measures the resistance of the thermistor 25, converts it to temperature data, and transmits the data to the detection signal processor 5.

[Step P4] The detection signal processor 5 gives the time lag remover 12 the impulse response coefficients N, $\alpha_n$ and $\tau_n$ of FPD 2 corresponding to the sensor temperature received from the sensor temperature measuring unit 4. Then, the operation returns to step P2 and the controller 26 checks whether a next predetermined time has arrived.

Thereafter, and until the next predetermined time, the time lag remover 12 performs time lag removing computations using the impulse response coefficients corresponding to the latest sensor temperatures measured by the sensor temperature measuring unit 4.

In the second embodiment, the operator inputs points of time for performing the sensor temperature measurement. Instead, the sensor temperature measurement may be performed on schedule information such as "9:00, 10:15, 13:00, and so on". Further, the operator may input "five minutes from now", for example.

In the second embodiment, as described above, the sensor temperature of FPD 2 is automatically measured every predetermined time. Temperatures may be measured accurately at all times without the operator forgetting to measure temperatures or making errors. As a result, time lags may be removed accurately from the impulse response, and corrected radiation detection signals have time lags removed with high accuracy.

In the first and second embodiments, various instructions of the operator are inputted to the operating unit 13, which are then transmitted to the main control unit 14.

This invention is not limited to the foregoing embodiments, but may be modified as follows:

(1) The first and second embodiments described above employ an FPD as the radiation detecting device. This invention is applicable also to an apparatus having a radiation detecting device other than an FPD that causes time lags in X-ray detection signals.

(2) While the apparatus in the first and second embodiments are fluoroscopic apparatus, this invention is applicable also to an apparatus other than the fluoroscopic apparatus, such as an X-ray CT apparatus.

(3) The apparatus in the first and second embodiments are designed for medical use. This invention is applicable not only to such medical apparatus but also to an apparatus for industrial use such as a nondestructive inspecting apparatus.

(4) The apparatus in the first and second embodiments use X rays as radiation. This invention is applicable also to an apparatus using radiation other than X rays.

(5) In the first and second embodiments, the thermistor is used for measuring the sensor temperature, without limiting the invention. The number of thermistors applied to the glass plate is not limitative, either. A single thermistor may be applied centrally of the glass plate, or a plurality of thermistors may be applied to several positions on the glass plate. A resisting element may be provided for each X-ray detecting element 2a of FPD 2 (FIG. 2), so that the temperature of each X-ray detecting element 2a may be measured by reading the resistance of the resisting element.

Figure 11:
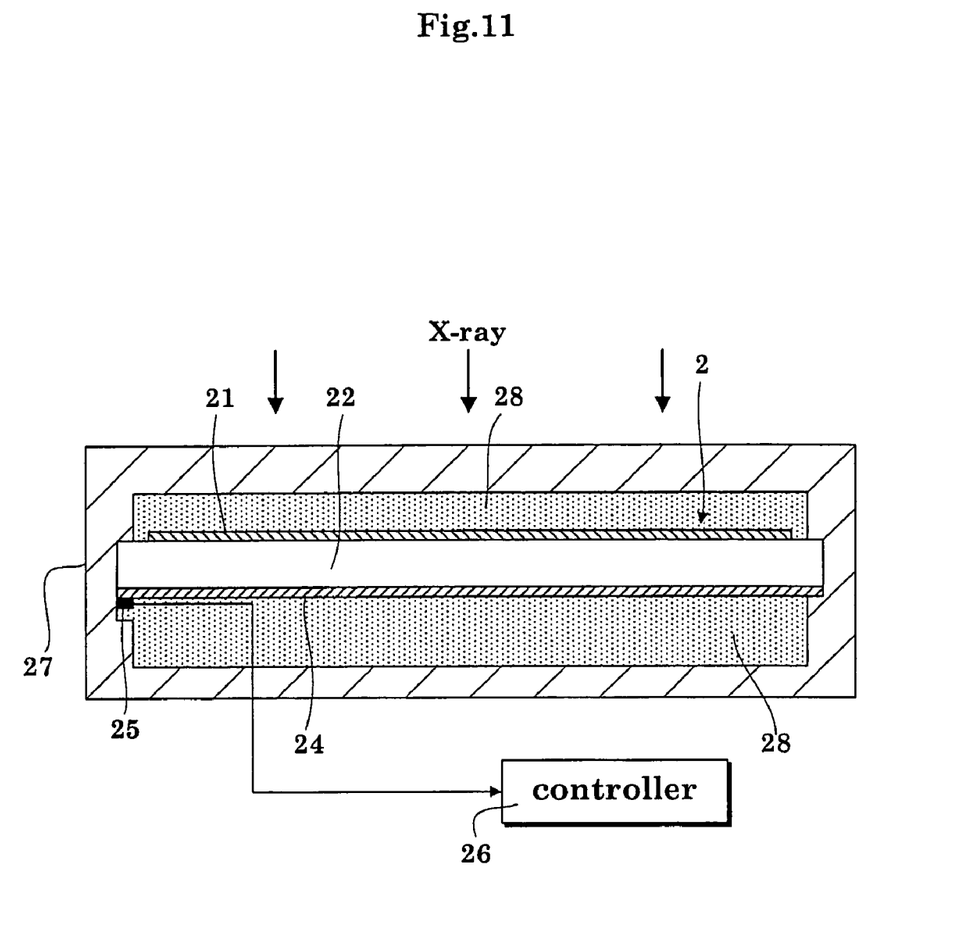
FIG. 11 is a view showing a modified position of a sensor temperature measuring unit.

As shown in FIG. 11, the FPD 2 including the voltage application electrode 21, semiconductor film 22, carrier collection electrodes 23 (not shown in FIG. 11) and glass plate 24 may be disposed in a housing 27 formed, for example, of aluminum, and a resin 28 poured into the housing 27 to mold the FPD 2 with the resin 28. In this case, the temperature measuring unit, typically the thermistor 25, may be enclosed in the resin 28, embedded in a lateral surface of the housing 27, and applied to the glass plate 24.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus having radiation emitting means for emitting radiation toward an object under examination, radiation detecting means for detecting radiation transmitted through the object under examination, and signal sampling means for taking radiation detection signals from the radiation detecting means at predetermined sampling time intervals, for obtaining radiographic images based on the radiation detection signals outputted from the radiation detecting means at the predetermined sampling time intervals as radiation is emitted to the object under examination, said apparatus comprising:

temperature measuring means for measuring temperature of said radiation detecting means; and time lag removing means for removing lag-behind parts from the radiation detection signals by a recursive computation, on an assumption that a lag-behind part included in each of said radiation detection signals taken at the predetermined sampling time intervals is due to an impulse response formed of one exponential function or a plurality of exponential functions with different attenuation time constants;
wherein said time lag removing means is arranged to determine said impulse response based on a result provided by said temperature measuring means, and obtain a corrected radiation detection signal by removing the lag-behind part based on said impulse response corresponding to said result.

2. A radiographic apparatus as defined in claim 1, wherein said temperature measuring means is arranged to measure temperature automatically at every predetermined time.

3. A radiographic apparatus as defined in claim 2, wherein said predetermined time is set by inputting a point of time for measuring said temperature.

4. A radiographic apparatus as defined in claim 2, wherein said predetermined time is set at time intervals having a fixed value.

5. A radiographic apparatus as defined in claim 2, wherein said predetermined time is set by schedule information containing points of time.

6. A radiographic apparatus as defined in claim 2, wherein said predetermined time is set by inputting a passage of time from a current point of time.

7. A radiographic apparatus as defined in claim 1, wherein said temperature measuring means is arranged to measure temperature upon an instruction for temperature measurement.

8. A radiographic apparatus as defined in claim 1, wherein said temperature measuring means is arranged to measure temperature automatically before an actual emission of radiation performed upon an instruction for emitting radiation.

9. A radiographic apparatus as defined in claim 1, wherein said radiation detecting means is a flat panel X-ray detector having numerous X-ray detecting elements arranged longitudinally and transversely on an X-ray detecting surface.

10. A radiographic apparatus as defined in claim 1, wherein impulse response coefficients corresponding to temperatures are determined based on a predetermined relationship between the temperature of said radiation detecting means and said impulse response coefficients, and results of measurement by said temperature measuring means.

11. A radiographic apparatus as defined in claim 1, wherein said radiation detecting means is a flat panel X-ray detector having numerous X-ray detecting elements arranged longitudinally and transversely on a radiation detecting surface, said flat panel X-ray detector including:
a semiconductor film which is an X-ray sensitive film for generating carriers in response to incident X rays;
a voltage application electrode disposed on an X-ray incident surface of said semiconductor film;
carrier collection electrodes arranged on a non-incident surface of said semiconductor film and acting as part of said X-ray detecting elements; and
a glass plate having said carrier collection electrodes vapor-deposited thereon;
said temperature measuring means including:
a thermistor applied to said glass plate; and
a controller for reading a resistance of said thermistor.

12. A radiographic apparatus as defined in claim 11, wherein said thermistor is applied centrally of said glass plate.

13. A radiographic apparatus as defined in claim 11, wherein a plurality of thermistors are applied to several positions on said glass plate.

14. A radiographic apparatus as defined in claim 1, wherein said radiation detecting means is a flat panel X-ray detector having numerous X-ray detecting elements arranged longitudinally and transversely on a radiation detecting surface, said temperature measuring means comprising resisting elements provided for said X-ray detecting elements, respectively.

15. A radiographic apparatus as defined in claim 1, wherein said time lag removing means is arranged to perform the recursive computation for removing the lag-behind part from each of the radiation detection signals, based on the following equations A–C:

$$X_k = Y_k - \sum_{n=1}^{N} \{\alpha_n \cdot [1 - \exp(T_n)] \cdot \exp(T_n) \cdot S_{nk}\} \quad \text{A}$$

$T_n = -\Delta t / \tau_n$ B $S_{nk} = X_{k-1} + \exp(T_n) \cdot S_{n(k-1)}$ C where $\Delta t$: the sampling time interval;
k: a subscript representing a k-th point of time in a sampling time series;
$Y_k$: an X-ray detection signal taken at the k-th sampling time;
$X_k$: a corrected X-ray detection signal with a lag-behind part removed from the signal $Y_k$;
$X_{k-1}$: a signal $X_k$ taken at a preceding point of time;
$S_{n(k-1)}$: an $S_{nk}$ at a preceding point of time;
exp: an exponential function;
N: the number of exponential functions with different time constants forming the impulse response;
n: a subscript representing one of the exponential functions forming the impulse response;
$\alpha_n$: an intensity of exponential function n; and
$\tau_n$: an attenuation time constant of exponential function n.

16. A radiographic apparatus as defined in claim 1, wherein said apparatus is a medical apparatus.

17. A radiographic apparatus as defined in claim 16, wherein said medical apparatus is a fluoroscopic apparatus.

18. A radiographic apparatus as defined in claim 16, wherein said medical apparatus is an X-ray CT apparatus.

19. A radiographic apparatus as defined in claim 1, wherein said apparatus is for industrial use.

20. A radiographic apparatus as defined in claim 19, wherein said apparatus for industrial use is a nondestructive inspecting apparatus.

21. A radiographic apparatus as defined in claim 1, further comprising a housing defining an interior therein for receiving said radiation detecting means, said interior containing a resin, said radiation detecting means being enclosed in said resin and embedded in said housing.

* * * * *